United States Patent [19]
Leucci

[11] 3,951,153
[45] Apr. 20, 1976

[54] SAFETY DEVICE FOR CATHETERS AND THE LIKE

[76] Inventor: Gino Leucci, Medford & Academy Roads, Philadelphia, Pa. 19154

[22] Filed: Feb. 4, 1975

[21] Appl. No.: 546,934

[52] U.S. Cl. .................. 128/349 R; 128/349 B; 285/260
[51] Int. Cl.² ........................................ A61M 25/00
[58] Field of Search ............... 128/247, 348–351; 285/260

[56] References Cited
UNITED STATES PATENTS

| | | | |
|---|---|---|---|
| 3,731,684 | 5/1973 | Spiegel | 128/247 X |
| 3,768,476 | 10/1973 | Raitto | 128/247 X |
| 3,805,794 | 4/1974 | Schlesinger | 128/349 R |
| 3,828,764 | 8/1974 | Jones | 128/350 R |
| 3,860,007 | 1/1975 | Binard et al. | 128/349 B |

*Primary Examiner*—Dalton L. Truluck
*Attorney, Agent, or Firm*—Ostrolenk, Faber, Gerb & Soffen

[57] ABSTRACT

A safety device for use with Foley catheters and the like to prevent internal lacerations of the bladder neck and urethra which may occur as a result of accidental dislocation of such catheters. A coupler assembly is utilized to join the previously severed sections of the catheter. Several axially aligned slits are made in one severed section of the catheter to form a plurality of strips. One hollow tubular projection of the coupler is fitted into the opening of this section whereupon the strips of this section of the catheter are inserted into anchoring notches to lock the coupler thereto. The remaining portion of the catheter is force fitted into an oppositely directed hollow tubular projection. Thus the first catheter section which is placed within the bladder of a patient, is free to remain seated within the bladder with the remaining section of the catheter being adapted to be released from the coupler without pulling the anchored catheter section out of the bladder.

The locking notches of the coupler also provide a fluid (i.e., water and/or air) tight seal for the fluid (i.e., water and/or air) passageway extending between the inflatable portion of the catheter and the air pressure input end to maintain the inflatable portion in the inflated condition thereby assuring proper placement of the catheter within the bladder.

6 Claims, 14 Drawing Figures

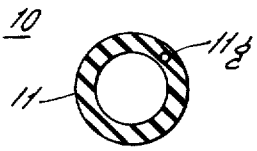
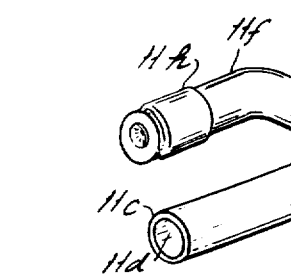
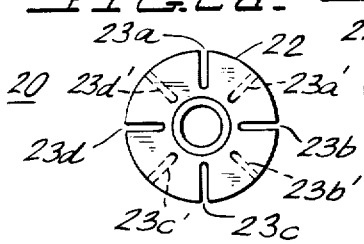
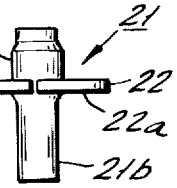
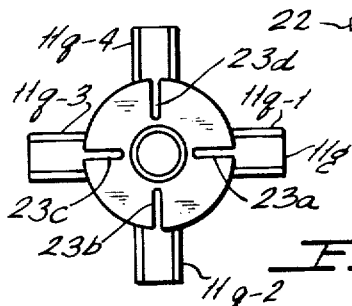
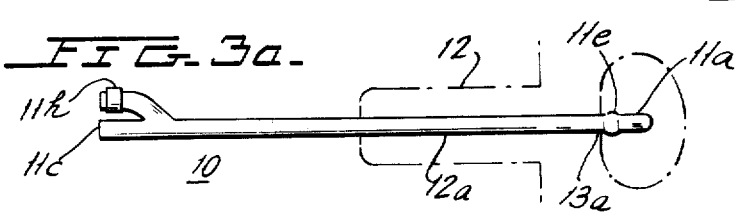
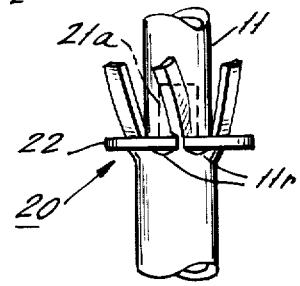
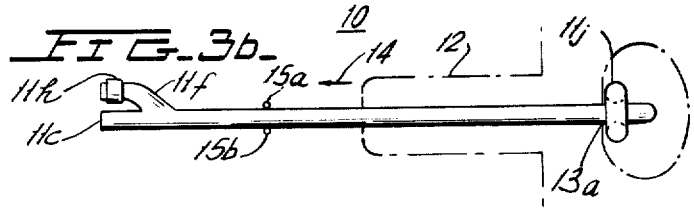
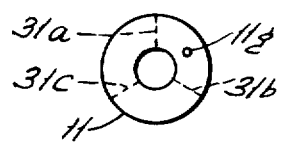
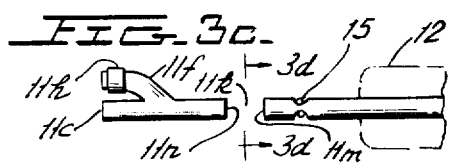
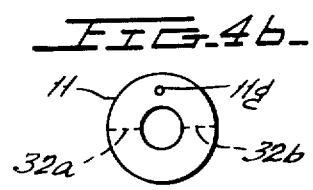
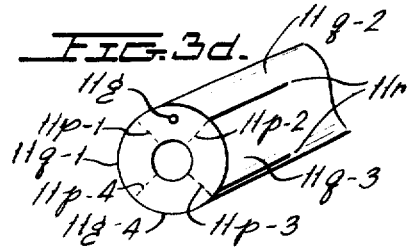
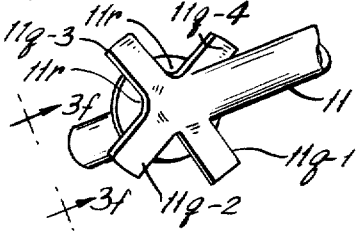

SAFETY DEVICE FOR CATHETERS AND THE LIKE

BACKGROUND OF THE INVENTION

The present invention relates to catheters and more particularly to a novel coupler for catheters and a method for using same so as to prevent internal injury to the patient as a result of such use.

Foley catheters are typically designed so that the tip which is inserted into the body communicates with the opposing end of the catheter through the hollow elongated interior of the tube for the drainage or removal of body fluids. In order to assure proper placement of the catheter within the body, an annular inflatable portion is spaced inwardly from the aforesaid tip, is normally deflated, and is inflated after insertion of the tip into the body such as, for example, the urinary bladder. The opposite end of the catheter is provided with a branch arm having a one-way valve structure through which fluid (i.e., water or air) under pressure may be admitted and which communicates with the inflatable annular portion through a narrow elongated passageway lying substantially parallel to the elongated hollow cylindrical interior. By insertion of either water or air under pressure in this manner, the annular portion, when inflated, assumes a substantially toroidal shape and, in the example wherein the Foley catheter is inserted into the urinary blader, serves to retain the tip of the catheter at the entrance of the urinary bladder when in the inflated condition, thereby assuring proper drainage through the opening provided at the tip and through its hollow interior to a waste container which may, for example, be strapped or otherwise affixed to the patient typically at or above the patient's knee.

The patient, upon entering or leaving the bed, may accidentally step upon the waste container or, frequently the waste container may become lodged or snagged upon a stationary member causing the Foley catheter to be pulled outwardly from its position. With the toroidal portion fully inflated, the pulling or dislodging of the Foley catheter from its location in the urinary bladder and through the urethra (urinary canal) will cause severe lacerations and inflict severe pain upon the patient, severe bleeding and the possibility of damage to the external urinary sphyncter with permanent urinary incontinence.

BRIEF DESCRIPTION OF THE INVENTION

The present invention is characterized by providing a novel coupler member for Foley catheters and the like. The coupler member is positioned at a location intermediate the ends of the Foley catheter and is adapted to enable a section of the Foley catheter communicating with the waste container to become relatively easily and rapidly disconnected from the section of the Foley catheter positioned within the urinary bladder in the event that the section of the catheter joined to the waste container is either accidentally or deliberately displaced from the remaining section so as to prevent the remaining section from being drawn out of the urinary bladder thereby preventing laceration of the urinary canal, severe bleeding, possible urinary incontinence, and attendant pain to the patient. The coupler is further provided with a circular shaped flange which is notched to permit strips of the severed end of the catheter having the insertable tip portion to be firmly anchored thereto so as to water or air-tightly seal the water or air passageway leading to the inflatable toroidal shaped portion of the catheter thereby maintaining the inflatable portion in its inflated position. The portion of the catheter which is joined to the waste container is force fitted upon an oppositely directed hollow cylindrical projection which is adapted to enable the section of the catheter joined to the waste container to be released from the coupler in the event that an either accidental or deliberate force is imparted thereto to pull this portion of the catheter away from the coupler enabling the portion of the Foley catheter inserted into the urinary bladder to remain in position and thereby prevent lacerations of the urinary canal, and the severe complications such as severe bleeding and permanent urinary incontinence.

BRIEF DESCRIPTION OF THE FIGURES AND OBJECTS OF THE INVENTION

It is therefore one object of the present invention to provide a novel coupler for use with Foley catheters and the like for joining two severed sections of the Foley catheter while enabling one of the severed sections to be releasably coupled therefrom to prevent disastrous lacerations of the urinary canal while further providing water or air tight seal for the water or air passageway utilized to introduce water or air into the inflatable portion so as to maintain the inflatable portion fully inflated in the event that the portion of the catheter joined to the waste container is either deliberately or accidentally removed from the coupler.

The above as well as other objects of the present invention will become apparent when reading the accompanying description and drawings in which:

FIG. 1 shows a perspective view of a Foley catheter.

FIG. 1a shows a sectional view of the catheter of FIG. 1 looking in the direction of arrows 1a—1a.

FIGS. 2a and 2b show top and end views, respectively, of a coupler for use with the catheter of FIG. 1.

FIGS. 3a–3h show views of the catheter and coupler of FIGS. 1–2b useful in describing the method of insertion of the catheter and the connection of the coupler with the catheter.

FIGS. 4a and 4b show sectional views of the severed catheter which are modifications of the view of FIG. 3d.

DETAILED DESCRIPTION OF THE INVENTION

FIGS. 1 and 1a show a Foley catheter 10 which is typically comprised of a slender elongated hollow tube 11 adapted for insertion into a body cavity for distending the passage or drawing fluid, especially for distending and/or drawing off urine from the bladder.

The free end 11a of tube 11 is provided with a pair of elongated openings 11b which are arranged in a diametrically opposed manner about the substantially cylindrical surface of tube 11 at the free end thereof. The opposite end 11c is adapted for connecting the hollow internal passageway 11d to a waste container in any suitable manner.

Spaced inwardly from tip 11a is a thin stretchable cylindrical shaped portion 11e which is joined to hollow tubular portion 11f by means of water or air passageway 11g shown best in FIG. 1a and extending from inflatable portion 11e along tube 11 and along branch tube 11f which is provided at its free end with a one-way valve structure 11h adapted to be coupled to a source of water or air for introducing water or air under pressure through one-way valve structure 11h, branch tube 11f and conduit 11g so as to inflate cylindrical portion 11e to form a substantially toroidal shaped inflated configuration 11j.

The manner of insertion, operation and use of the catheter 10 can best be understood from a consideration of FIGS. 3a and 3b. Tip 11a is introduced into the male organ 12 and is passed along the canal 12a and into the bladder 13 by a distance sufficient to assure that band 11e extends beyond the opening 13a of bladder 13. Thereafter, water or air under pressure is introduced into one-way valve 11h, branch 11f and air passage 11g causing band 11e to become inflated and assume the toroidal shaped configuration 11j of FIG. 3b. Catheter 10 is then pulled or otherwise moved in the direction shown by arrow 14 to position and seat the inflated portion 11j at the mouth 13a of bladder 13. The source of water or air under pressure may be removed since one-way valve 11h assures air-tight sealing of conduit 11g. End 11c of tube 11 is joined to the mouth or opening of a waste container (not shown for purposes of simplicity) to permit urine or other body fluids to be drained from the bladder and through the catheter into the waste container which may either be suspended from a bed or which may be strapped to the leg of an ambulatory patient.

A coupler 20 of the present invention which is shown best in FIGS. 2a and 2b, is utilized to prevent catheter 10 from being accidentally removed from bladder 13 and canal 12a when band 11e is in the inflated position 11j so as to prevent internal lacerations and attendant pain.

Coupler 20 is comprised of a hollow elongated tubular member 21 having a circular shaped flange 22 positioned intermediate the ends of tubular member 21 so as to define first and second tubular portions 21a and 21b extending outwardly in opposing directions from flange 22. Flange 22 is provided with a plurality of narrow radially aligned notches 23a–23d which extend inwardly from the periphery of flange 22 and which are adapted to anchor one portion of the catheter in a manner to be more fully described.

The manner in which the coupler is joined to the catheter is as follows:

The Foley catheter is inserted, inflated and appropriately positioned within a urinary bladder in the same manner as was described hereinabove with reference to FIGS. 3a and 3b. After the catheter is appropriately positioned with the inflatable section 11e fully inflated to assume the configuration as shown at 11j in FIG. 3b, a clamp, shown schematically and designated by numeral 15 of FIG. 3b, is applied to tube 11 at a location displaced from the free end of male or female urinary system (meatus) 12. The clamp is squeezed in a direction shown by arrows 15a and 15b so as to assure water or air-tight sealing of water or air passageway 11g to maintain portion 11j inflated.

With the clamp 15 in the position shown in FIG. 3c, catheter 10 is severed at location 11k which is preferably a suitable distance from the location of clamp 15.

The severed end 11m of the catheter portion inserted into the male or female urinary canal 12 is then cut or severed by means of surgical scissors at the four positions indicated by dotted lines 11p. The four cuts 11p may be formed by two separate cutting operations in which the severed end 11m is observed and a first cut is made so as to sever the tube along dotted lines 11p-1 and 11p-2, with the cuts being made to assure that cut 11p-1 is clearly displaced from water or air passageway 11g. Thereafter a second single cut is made to sever tube 11 along dotted lines 11p-3 and 11p-4 again with sufficient care being exercised to assure that the cut made along dotted line 11p-4 is clearly displaced from water or air passageway 11g.

The depth of each cut is preferably of the order of ½ inch in order to form four severed strips 11q-1 through 11q-4 of substantially equal quadrants of a circle each strip having an axial length of the order of ½ inch.

Thereafter, tubular portion 21b of coupler 20 is inserted into opening 11d in severed portion 11m until the ends 11r of the cuts engage the surface 22a of flange 22 as is shown best in FIGS. 2b and 3c. The orientation of coupler 20 in tube 11 is such that the notches 23a–23d are preferably each aligned with one of the strips 11q-1 through 11q-4 respectively. FIG. 3e shows the coupler 20 fully inserted into the catheter's severed end 11m and FIG. 3f, which is a view looking in the direction of arrows 3f—3f of FIG. 3e, shows the alignment of the strips 11q-1 through 11q-4 with the notches 23a–23d respectively.

With the the notches and strips in alignment as shown in FIG. 3f, each of the strips 11q are forced into an associated one of the narrow notches 23a–23d so as to firmly anchor the coupler 20 to the catheter section which has been inserted into the bladder 13.

In order to assure that the air passageway 11g will be air-tightly sealed, strip 11q-1 may be twisted at least once before insertion into notch 23a. The width of the notches 23a–23d is adapted to assure that each of the strips 11q inserted therein will be pinched and hence firmly force fitted within an associated notch to firmly anchor coupler 20 to the catheter portion as well as assuring that the air passageway 11g in strip 11q-1 is air-tightly sealed.

Upon completion of this operation, clamp 15 may be removed since notch 23a air-tightly seals water or air passageway 11g. FIG. 3g shows the strips 11q-1 through 11q-4 after insertion into the notches 23a–23d.

Thereafter, severed end 11n of the remaining portion of catheter 10 (see FIGS. 3c and 3g) is positioned immediately above tubular portion 21a of coupler 20 and is force fitted upon tubular portion 21a until end 11n abuts against surface 22b of flange 22, FIG. 3h showing the catheter portions in the fully assembled position.

After assembly of the coupler to the catheter, and 11c may be joined to a waste container (not shown for purposes of simplicity) to permit drainage of the bladder and sanitary collection of waste matter.

In the event that either the waste container or the section of the catheter joined to tubular portion 21a is pulled in the direction away from the male organ 12, the force fitting between tubular portion 21a and end 11n is adapted to permit the catheter portion connected to tubular portion 21a to be released therefrom without removing the portion of the catheter anchored within bladder 13 thereby preventing any internal lacerations. The coupling of the catheter may be simply done by forcibly remounting end 11n of the catheter to the tubular portion 21a.

It can be seen from the foregoing description that the present invention provides a novel coupler for use with Foley catheters and the like wherein the coupler is adapted to be firmly anchored to the portion of the catheter positioned within the bladder while permitting the remaining portion of the catheter to be releasably secured therefrom to prevent the bladder in the urinary canal from being lacerated. The coupler, in addition to being anchored to the portion of the catheter inserted within the bladder, further serves to air-tightly seal the water or air passageway of the catheter inflatable portion 11e to prevent uncessary removal or dislodging of the catheter from its proper position.

While a particular embodiment of the invention has been described, it is appreciated that changes and variations are possible and it is desired to cover all such modifications of the invention as would be apparent to one skilled in the art. For example, the flange 22 of coupler 20 need not be provided with a circular periphery but may be provided with a polygonal periphery which may be triangular, square, pentagonal and so forth.

Also, while the preferred coupler is shown as being provided with four notches 23a–23d, a greater or lesser number of notches may be provided if desired. For example, considering FIG. 4a, and in the event that only three notches are provided in flange 22, tubular portion 11 may be severed along the three imaginary lines 31a, 31b and 31c. As a further alternative, and in the event that flange 22 is provided with only two notches, tubular portion 11 may be severed along the dotted lines 32a and 32b as shown in FIG. 4b. As a further alternative, flange 22 may be provided with the four notches 23a–23d as shown and tubular portion 11 may be severed in the manner shown in either FIG. 4a or 4b whereby less than all of the four notches may be employed, if desired. As a further alternative, and in order to facilitate accurate location of air passageway 11g for purposes of assuring proper positioning of the cutting of the tubular member, a thin axial line 11t (see FIG. 1) may be provided along the exterior surface of tubular member 11 and parallel to air passageway 11g to thereby facilitate accurate location of the water or air passageway 11g after severing of the catheter at the location 11k shown in FIG. 3c so as to assure that the axial cuts formed in the tubular member are sufficiently displaced from the air passageway 11g.

As a further alternative embodiment of the invention, the coupler flange 22 may be provided with an additional set of notches 23a'–23d' as shown best in FIG. 2a in applications wherein it may be desired to firmly anchor adjacent end sections of a catheter or other flexible tubing where releasable couplings may not be necessary. The use of the alternative embodiment would be substantially similar to that described hereinabove with the exception that both end sections to be joined would be severed to form strips in the manner shown in FIGS. 3e and 3f and that the strips of one section would be force-fittingly inserted into the notches 23a–23d while the strips formed in the other section being joined would be force-fittingly inserted into the notches 23a'–23d'.

What is claimed is:

1. In combination, first and second resilient tubular sections and means for coupling the ends of said first and second resilient tubular sections, said first section having a plurality of axially aligned slits for dividing the end portion thereof into a plurality of strips, said means comprising:

a rigid tubular member adapted to have the opposite ends thereof press-fitted into the ends of the tubular sections to be joined;

a thin flange surrounding and extending outwardly from the exterior surface of said rigid member, said flange being located intermediate the ends of said rigid member;

said flange having a plurality of narrow notches extending inwardly from the periphery of said flange each being adapted to force-fittingly receive an associated one of said strips to anchor said coupling means to said first tubular section;

the press-fitting connection between said coupling means and said second tubular section being adapted to be released when said first and second sections are displaced from one another to prevent any displacement of said first tubular section as a result of any pulling force exerted upon said second tubular section.

2. The means of claim 1 wherein said first tubular section is further provided with an axial narrow diameter fluid passageway displaced from the hollow opening in said tubular section and substantially parallel thereto, said passageway extending into one of said strips;

said fluid passageway being fluid-tightly sealed by said coupling means by virtue of the force-fitting of the strip containing the fluid passageway within an associated one of said notches.

3. The means of claim 2 wherein said first tubular section is a Foley catheter further including an inflatable annular section adjacent the end of said first tubular section remote from said strips for assuring proper positioning of the catheter in a body cavity, said coupling means assuring that the inflatable annular section is maintained in the inflated state even though said second tubular section be released from said coupling means.

4. Means for coupling the ends of first and second resilient tubular sections, said first and second sections each having a plurality of axially aligned slits for dividing their end portions into a plurality of strips, said means comprising:

a rigid tubular member adapted to have the opposite ends thereof press-fitted into the ends of the tubular sections to be joined;

a thin flange surroudning and extending outwardly from the exterior surface of said rigid member, said flange being located intermediate the ends of said rigid member;

said flange having first and second groups of narrow notches extending inwardly from the periphery of said flange, the notches of said first and second groups being adapted to force-fittingly receive an associated one of the strips of said first and second resilient sections, respectively, to anchor said coupling means to said first and second tubular sections and thereby provide a substantially fluid-tight coupling.

5. A method for releasably joining a coupler to a Foley catheter said coupler being comprised of a rigid tubular member having a notched flange arranged about the periphery thereof and intermediate the ends thereof, and said catheter being comprised of an elongated flexible tube having a tip end adapted for insertion into a body cavity and a delivery end for communication with a waste receptacle, said catheter further having an annular inflatable section spaced inwardly from said tip end and communicating with a fluid input valve adjacent the delivery end by means of an axially aligned fluid passageway of narrow diameter displaced from the central opening of the flexible tube, said method comprising the steps of:

a. inserting the tip end into the desired body cavity;

b. introducing a fluid under pressure into said valve to inflate the inflatable section;

c. clamping said catheter flexible tube at a location exterior to the body of the patient to fluid-tightly seal the fluid passageway;

d. severing the tube at a position between the location of the clamped portion of the tube and the delivery end;

e. forming a plurality of axial slits in the section of tube adjacent to the clamped location and extending inwardly from the end of the severed tube section extending from the patient's body and towards the clamped portion thereby forming a plurality of slits;

f. force fitting one end of the rigid tube into the tube section extending from the patient's body until the ends of said slits are immediately adjacent said flange;

g. force-fitting inserting each strip into one of said notches to firmly anchor the coupler to the tube section and to fluid-tighly seal the fluid passageway;

h. unclamping the flexible tube;

i. force-fitting the opposite end of the coupler into the end of the tube section previously severed as per step (d).

6. The method of claim 5 futher comprising the step of coupling the delivery end of the catheter to a container.

* * * * *